United States Patent
Twisselman

[11] Patent Number: 5,861,983
[45] Date of Patent: Jan. 19, 1999

[54] MICROSCOPE FOR MICROSURGERY

[75] Inventor: Lorenz Twisselman, Prisdorf, Germany

[73] Assignee: J. D. Moller Optische Werke GmbH, Wedel, Germany

[21] Appl. No.: 941,220

[22] Filed: Oct. 1, 1997

Related U.S. Application Data

[63] Continuation of Ser. No. 788,920, Jan. 24, 1997, abandoned, which is a continuation of Ser. No. 498,136, Jul. 5, 1995, abandoned, which is a continuation of Ser. No. 56,509, May 3, 1993, abandoned.

[30] Foreign Application Priority Data

May 6, 1992 [DE] Germany ............... 92 05 870.1 U

[51] Int. Cl.⁶ .................................. G02B 21/00
[52] U.S. Cl. ............... 359/384; 359/368; 359/382
[58] Field of Search .................. 359/372–384, 359/368, 430; 248/123.1, 123.11, 280.11, 281.11

[56] References Cited

U.S. PATENT DOCUMENTS

| | | | |
|---|---|---|---|
| 4,035,057 | 7/1977 | Klein | 359/384 |
| 4,867,405 | 9/1989 | Nakamura | 359/384 |
| 5,052,789 | 10/1991 | Kleinberg | 359/375 |

FOREIGN PATENT DOCUMENTS

| | | | |
|---|---|---|---|
| 1217099 | 5/1966 | Germany | 359/377 |

*Primary Examiner*—Thong Nguyen
*Attorney, Agent, or Firm*—Friedrich Kueffner

[57] ABSTRACT

In order to minimize the requsite expenditure of energy involved in a positional change of a microscope for the microsurgery mounted on a floor stand or suspended from a ceiling suspension mount that comprises a viewing element (17, an eyepiece (12), an objective (13), a beam divider (11) disposed between the viewing element (17) and a magnification power changer (12), in which the microscope is swivelably disposed in a suspension mount in such a way that a microscope swivel axis is located in the beam divider exit axis (A), the point of intersection of the microscope swivel axis (B) and the beam divider exit axis (A) is located at the center of gravity or within the immediate proximity of the center of gravity of the microscope (Fig.).

14 Claims, 7 Drawing Sheets

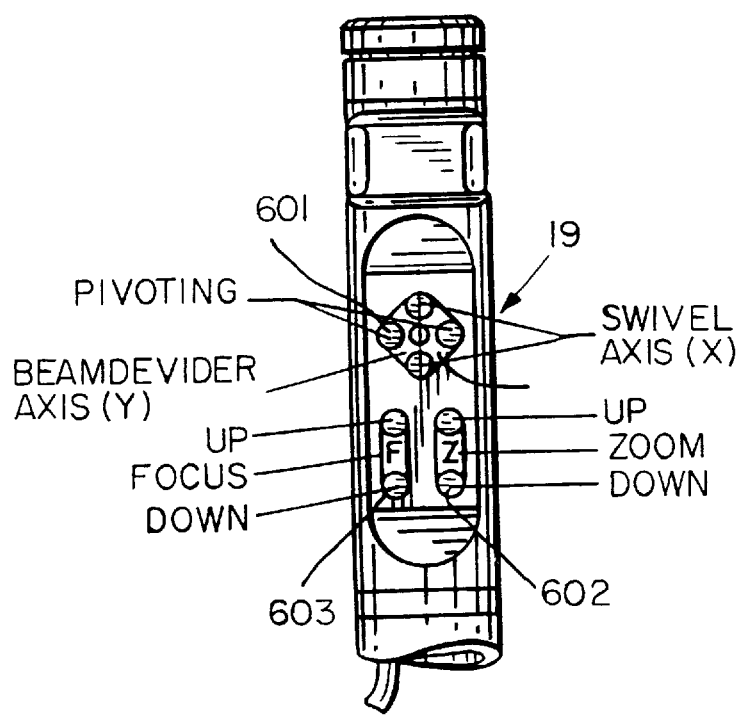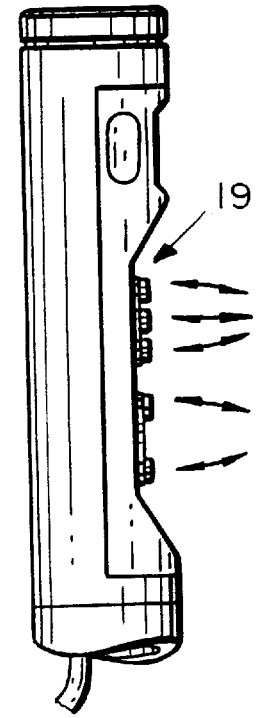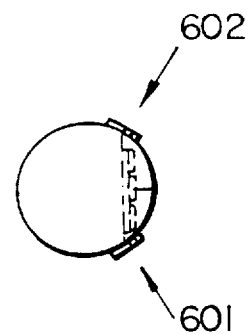
FIG.6A   FIG.6B
FIG.6C

MICROSCOPE FOR MICROSURGERY

This is a continuation of application Ser. No. 08/788,920 filed Jan. 24, 1997 which is a continuation of application Ser. No. 08/498,136 filed Jul. 5, 1995 which is a continuation of application Ser. No. 08/056,509 filed May 3, 1993, all abandoned.

BACKGROUND OF THE INVENTION

1. Field of the Invention

The present invention relates to a microscope for microsurgery mounted on a floor stand or suspended from a ceiling mount, with a viewing element, an eyepiece, an objective, a beam divider disposed between the viewing element and a magnification power changer, in which the microscope is swivelably disposed in a mounting bracket or suspension mount in such a way that a microscope swivel axis lies in the beam divider exit axis.

2. Description of the Related Art

Already in U.S. Pat. No. 4,035,057, such a microscope is described which is comprised of a plurality of modularly assembled elements whose selection is adapted to the specific requirement or purpose. Depending on additional peripheral equipment, microscopes are constantly becoming more voluminous and heavier, for which reason operating microscopes, as a rule, are mounted or suspended from suspension mounts, in many cases on the ceiling. This also facilitates the incorporation of an electromotive positional adjustment means, which is also used for focusing.

In order to make certain that additional supports components, such as cameras, movie cameras or television cameras or other co-viewer devices do not constitute an obstruction for the microscope operator when the microscope is swiveled, it is proposed in the U.S. Pat. No. 4,035,057 to swivelably dispose the microscope in a suspension mount, in which case the microscope swivel axis is Located in the beam divider exit axis. It is ensured in particular hereby that the additional supports components, such as cameras or movie cameras or such like, when the microscope is swiveled, have merely to be rotated but not displaced longitudinally, which would require an additional expenditure of energy.

The technical problem of the present invention consists in developing further the aforementioned microscope for microsurgery to the effect that the expenditure of energy necessary for a positional change of the microscope is minimized further so that the handling of the microscope is simplified.

SUMMARY OF THE INVENTION

This technical problem is resolved in the microscope described above in that the point of intersection of the microscope swivel axis and of the beam divider exit axis is located at the center of gravity or within the immediate proximity of the center of gravity of the microscope. The advantage of this step resides in that it is possible to adjust the microscope without it being necessary to perform any more substantial lifting operations.

According to a further development of the invention, the microscope is so as to be pivotable about the microscope swivel axis and/or the beam divider exit axis. These axes extend at an angle of 90° relative to each other.

More particularly, the microscope is swivelably hinged to a support, whose oppositely located end, for this articulated attachment, is constructed in the form of a swivel joint. The support substantially bridges the distance between the suspension point of the microscope and the microscope itself which has to be available at the position of the operating surgeon.

Structurally, the swivel joint mentioned is in the simplest manner by a lockable clevis pin connection and a suspension mount that is rotatable about a vertical axis.

By preference, the support is comprised of two essentially parallel side pieces which can be constructed in the form of hollow sections of lightweight construction. Preferably, at least one of the side pieces is capable of accommodating the control means of the electric actuation of the microscope functions such as, a drive of the zoom, a drive of the optical focus as well as the drive for pivoting the microscope about the microscope swivel axis and the beam divider exit axis.

According to another construction of the invention, the support is provided with a transverse adjustment means for the displacement of adjoining support components such as, movie cameras, television cameras or other co-viewer devices, in the horizontal direction to the longitudinal axis of the support. This transverse displacement renders the elimination of an imbalance due to laterally disposed accessories possible. The transverse adjustment means, may be a dovetail guideway.

According to a further construction of the invention, for swiveling the microscope about all possible axes of rotation, viz. the beam divider exit axis, the microscope swivel axis as well as the vertical axis of rotation, handles are provided on the suspension mount on the microscope which, preferably in the proximity of the center of gravity of the microscope, are disposed on the external body of the same. Further operating facilities result from the circumstance that electric drive means for swiveling the microscope about these axes are provided. By preference, the electric drive means can be activated with the aid of one of the handles stated.

In order to prevent an inadvertent swiveling of the microscope about one of the axes at the suspension fulcrum, the suspension mount is equipped with an electrically releasable brake.

According to a further embodiment of the invention, the electric drive means are constructed in such a way that they can be engaged and disengaged so that it is just as possible to also effect the swiveling and displacement of the microscope manually.

BRIEF DESCRIPTION OF THE DRAWING

FIG. 6 is a front, side and top view of a handle of the microscope of FIG. 1 having means for activating the electric drive means;

DETAILED DESCRIPTION OF THE PREFERRED EMBODIMENT

Figure 1:
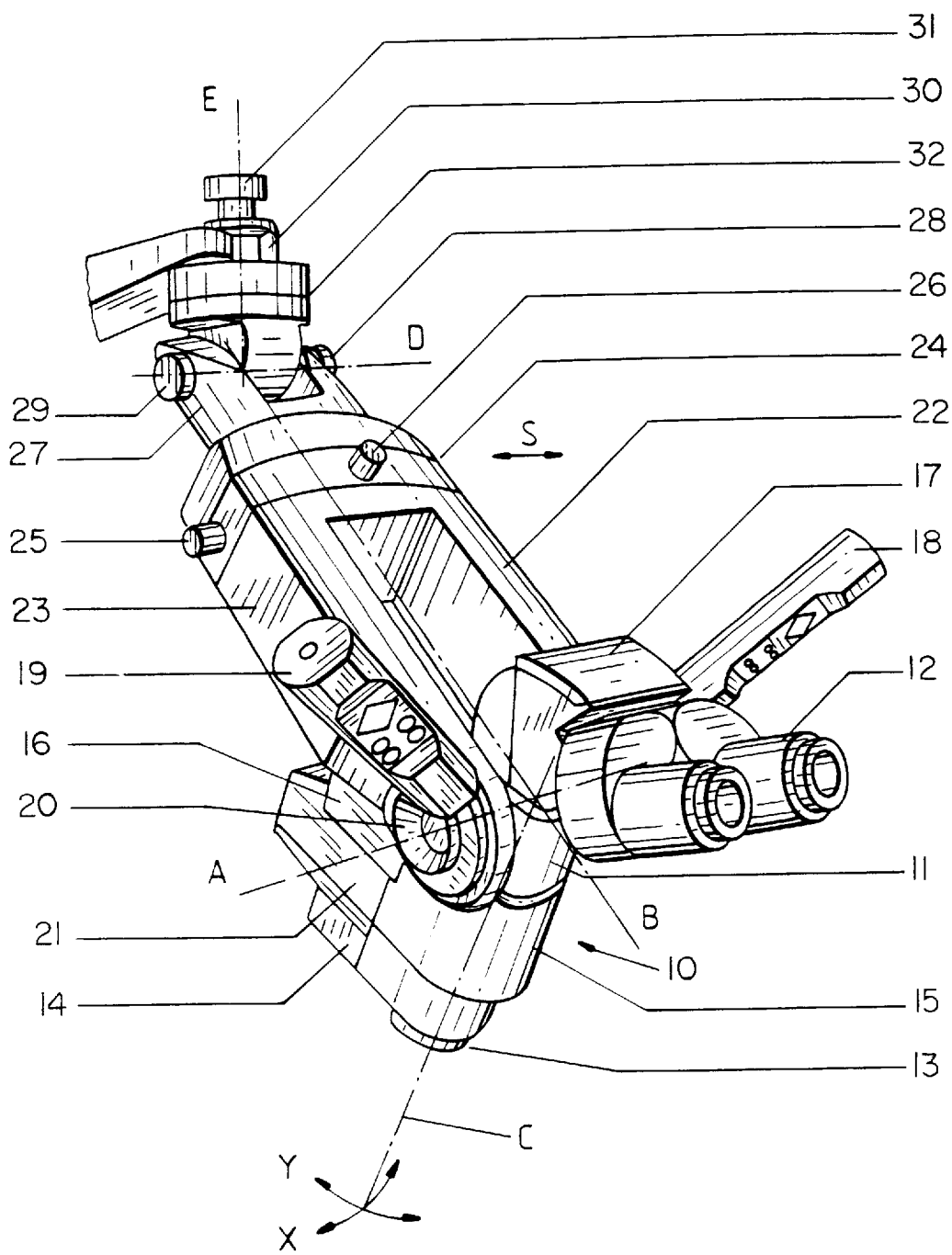
FIG. 1 is a perspective view of a microscope for microsurgery suspended from a ceiling.
Figure 2:
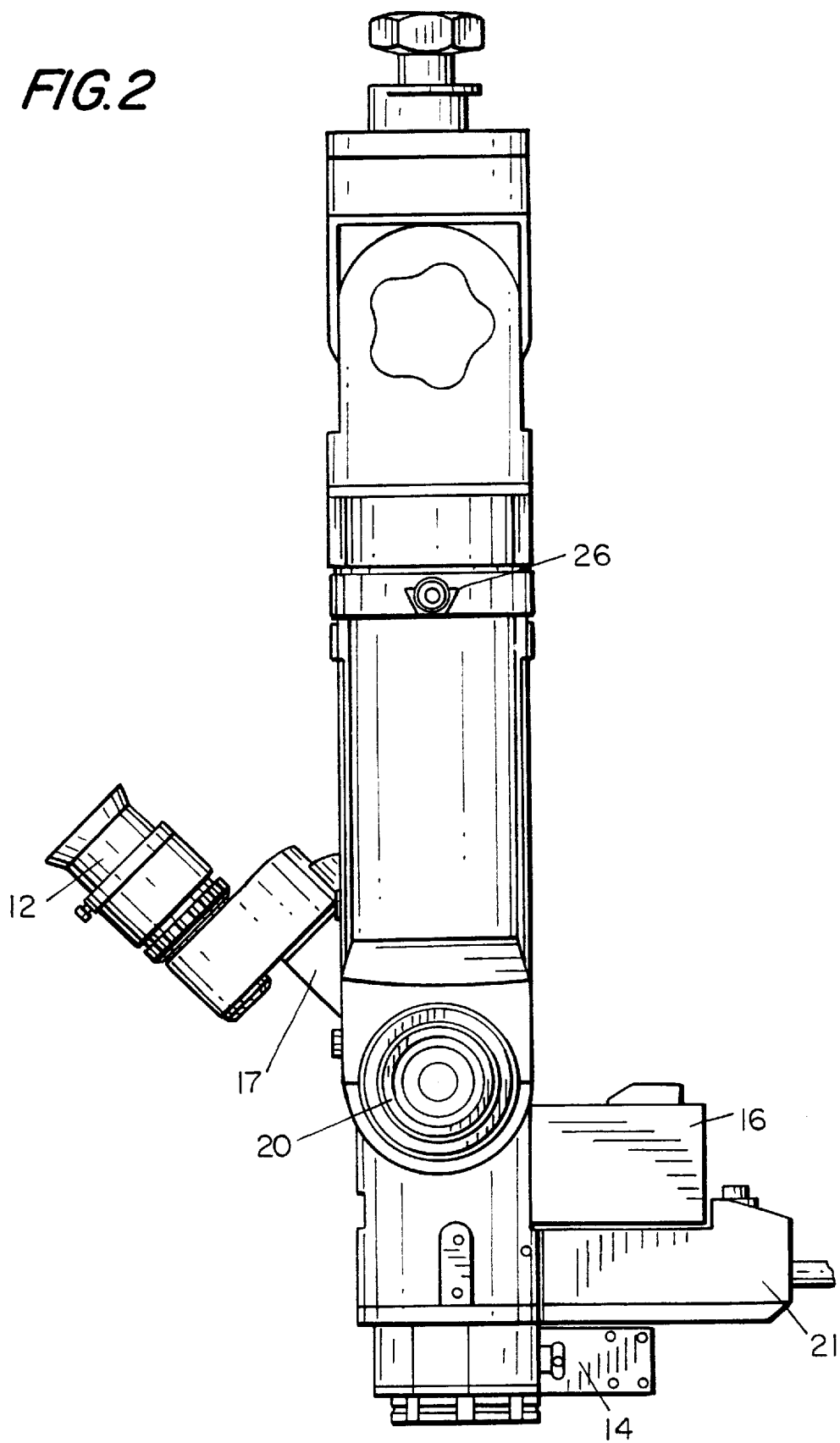
FIG. 2 is a side view of the microscope of FIG. 1.
Figure 3:
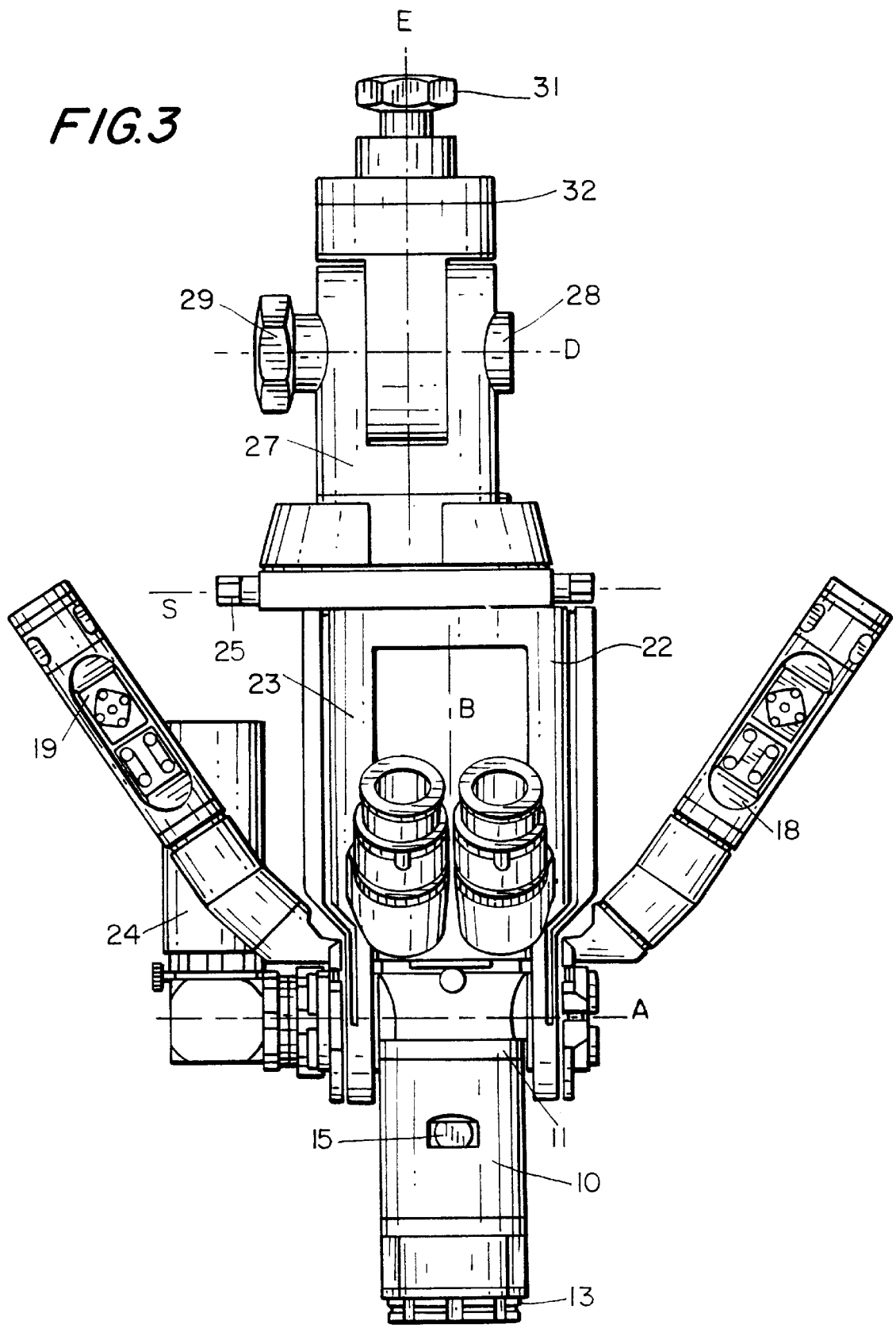
FIG. 3 is a front view of the microscope of FIG. 1.
Figure 4:
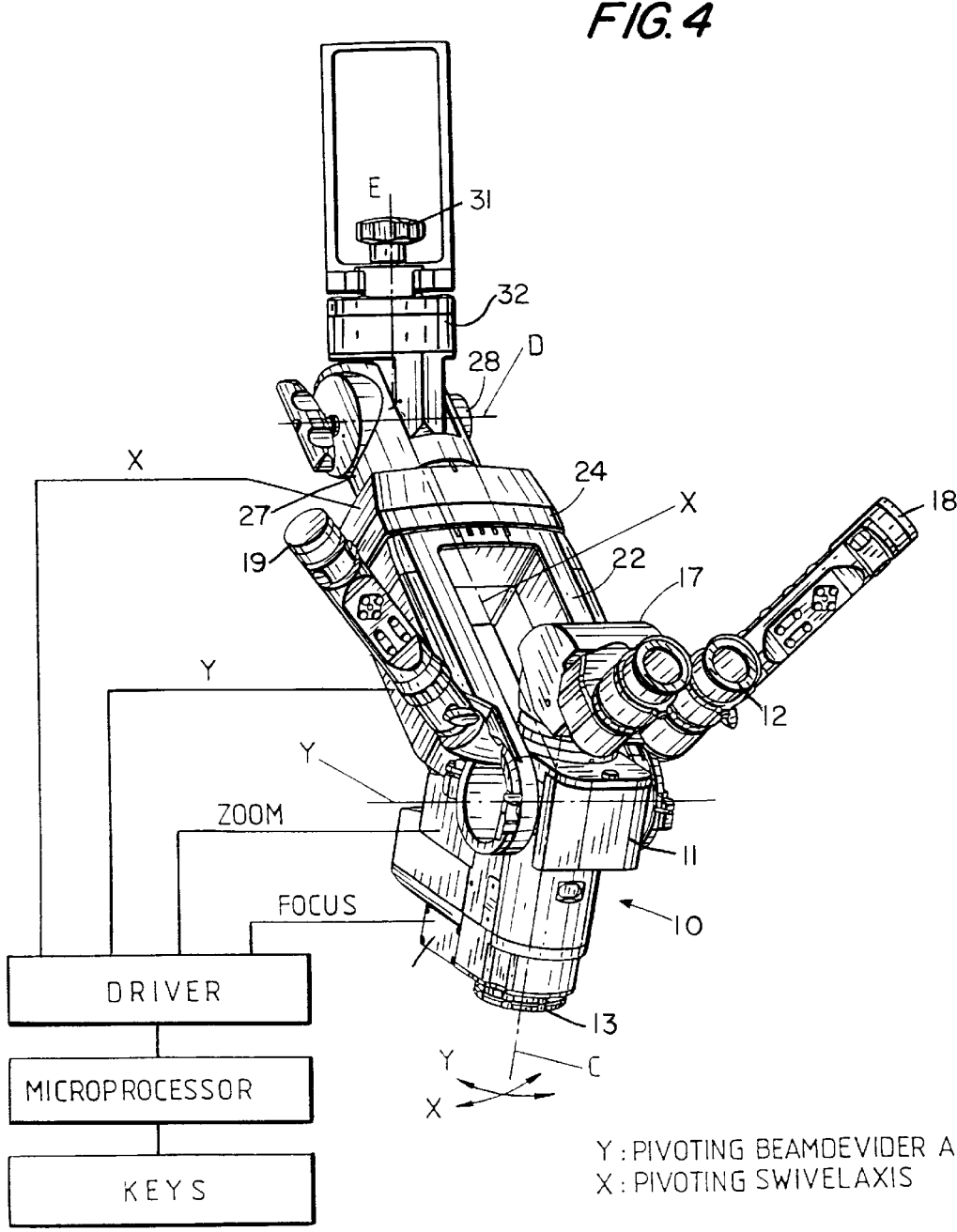
FIG. 4 is a perspective view of the microscope of FIG. 1.
Figures 5A, 5B:
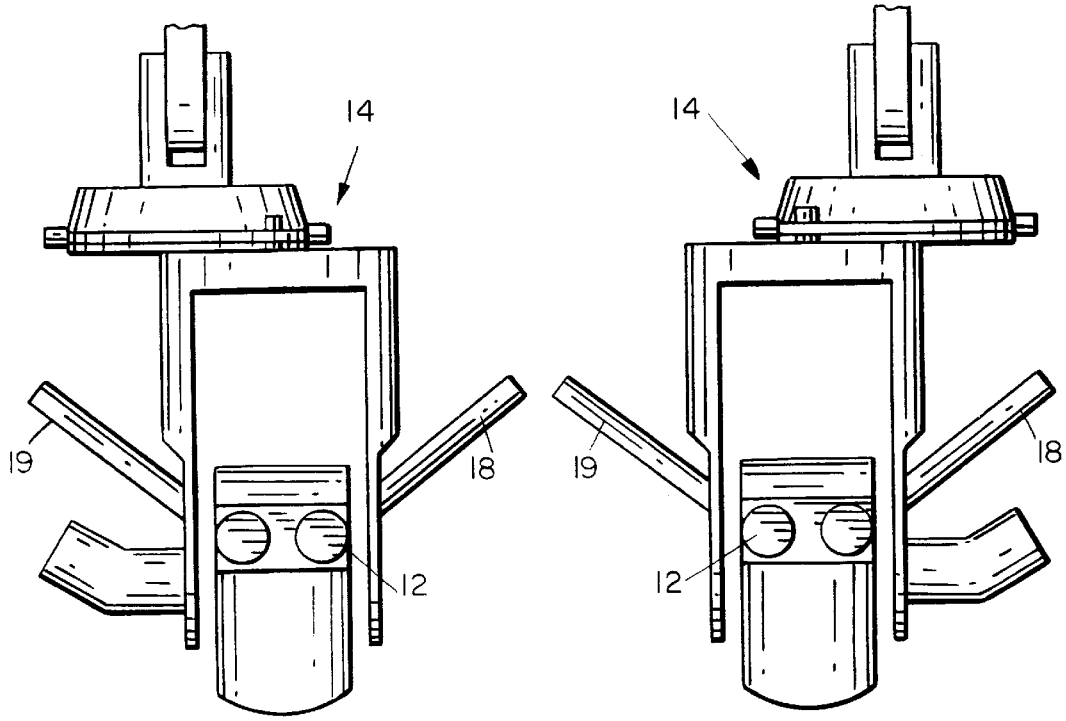
FIG. 5 is a view of the electric drive means of the microscope of FIG. 1, the microscope being swiveled and/or displaced.
Figure 8:
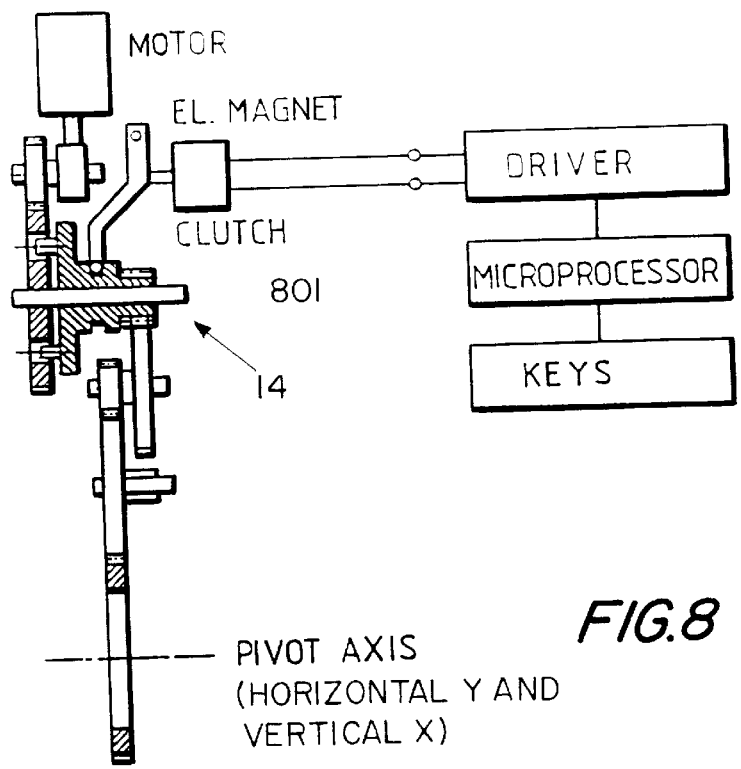
FIG. 8 is an interior view of the electric drive means of the microscope of FIG. 1, showing means for engaging and disengaging the electric drive means.
Figure 7:
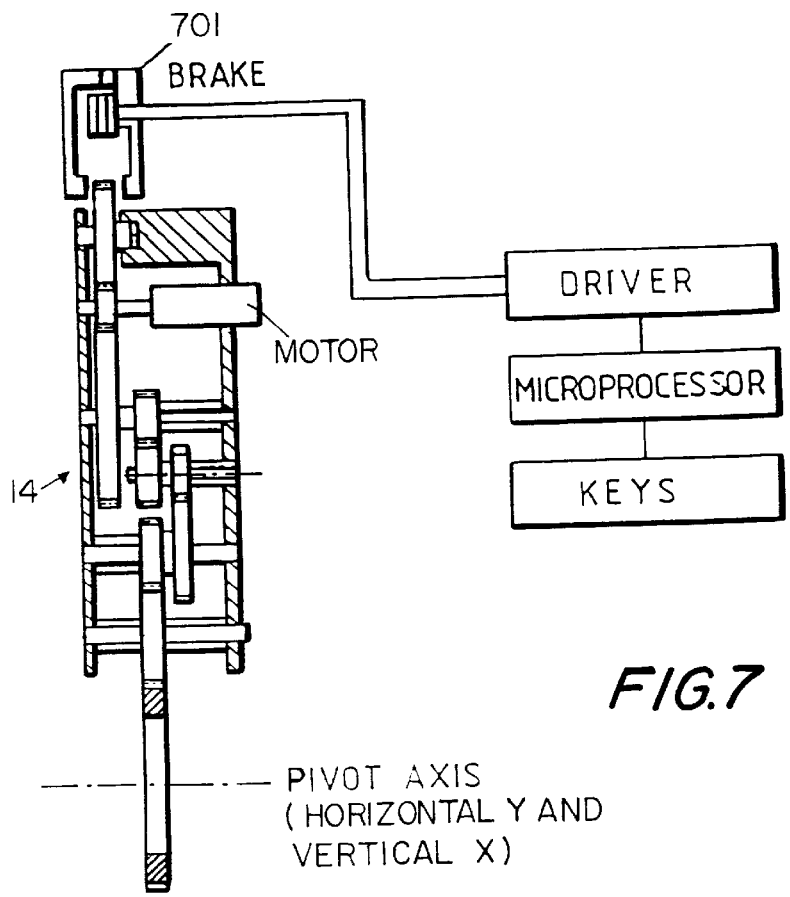
FIG. 7 is an interior view of the electric drive means of the microscope of FIG. 1, showing an electrically releasable break.

The microscope shown in the drawing includes the microscope housing 10 with a beam divider 11, the eyepieces 12 and the objective 13 or a group of objectives with a drive means 14 provided for this. Furthermore, the objective is provided with a zoom means 15 with the zoom drive means 16 provided for the Latter. In addition, a viewing element 17 is provided between the two handles 18 and 19. At the beam divider exits 20 which are Located on both sides of the microscope, cameras and movie cameras can be mounted. As a rule, the microscope is additionally provided with a coaxial illuminating means 21. The microscope is constructed in such a fashion that the point of intersection of the microscope swivel axis B and the beam divider exit axis A are Located at the center of gravity or within the immediate proximity of the center of gravity of the microscope. The longitudinal axis of the microscope is identified with C and passes Likewise through the joint point of intersection of the axes A and B. The microscope body 10 is articulately connected by means of two side pieces 22 and 23, in which case the end of the side pieces is provided with a dovetail guideway 24 which renders a transversal adjustment of th e side pieces with respect to the swivel axis B possible. This transverse adjustment can be actuated by means of the rotating knob 25 and arrested by means of the interlock 26. The support constituted of the side pieces 22 and 23, at the point of suspension, passes into a fork 27 which forms part of the swivel joint 28 which can be actuated by means of the rotating knobs 29. The swivel joint renders swiveling motions of the side pieces 22 and 23 about the axis of rotation D possible. Moreover, the suspension mount possesses an accommodation 30 with a rotating knob 31, which makes a swiveling of the microscope about the vertical axis E possible. An electrically releasable brake 701 is provided in the housing 32.

The described microscope can be operated as detailed in the following.

By being mounted so as to be pivotable about the axes A and B, it is possible for the microscope to be rotated in these axes for a rapid adjustment both manually and, for a fine adjustment, electromotively as well, for which purpose the handles 19 and 18 may be used. The position of these handles relative to the microscope is likewise adjustable. For the electromotive adjustment, a motor with gearing is incorporated into the left-hand side piece 23, which is capable of rotating the microscope about the axis A. In the transverse bar, a pertinent assembly for the rotation about the axis B is provided. The side piece 22 comprises the circuit boards of the electronics for the "intelligent" activation of all microscope functions. The gears can be disengaged by means of keys 801 in the handles 18 and 19 so that the microscope is freely rotatable manually about both axes A and B. When the motors are engaged, the electromotive movements can be controlled with the aid of keys or electric drive means 601, 602 and 603 provided in the handles 18, 19 or by a joystick of the foot-operated switch.

In the various positions assumed by the microscope when rotating about the gimbal frame axes A and B, in order to achieve an as good as possible approximated Cartesian xy motion in the focus with the swiveling of the microscope axis C, the suspension mount can be preadjusted about the axis D. The two axes B and C should preferably form an approximated right angle. In order to compensate a Lateral imbalance on the microscope caused by possible accessory components, the axis B can be displaced by one value, for which purpose the dovetail guideway 24 between the bifurcate transverse bar and the Lower portion of the swivel joint 28 may be used.

What is claimed is:

1. A surgical microscope mounted on a suspension mount, the microscope comprising a viewing element, two eyepieces an objective, a beam divider having a beam divider exit axis disposed between the viewing element and a magnification power changer, the microscope having an inclination axis and a swivel axis extending at a right angle to the beam divider exit axis, the microscope being mounted such that the inclination axis of the microscope coincides with the beam divider exit axis, the microscope having a center of gravity, wherein a point of intersection of the microscope swivel axis and the beam divider exit axis is located in the center of gravity of the microscope or within the immediate proximity of the center of gravity of the microscope, and wherein the microscope is mounted in the suspension mount so as to be pivotable about the microscope swivel axis and about the beam divider exit axis.

2. The microscope according to claim 1, wherein the microscope is swivelably hinged onto a support, and wherein an oppositely located end of the support is constructed in the form of a swivel joint.

3. The microscope according to claim 2, wherein the swivel joint comprises a lockable clevis pin connection and a suspension mount that is rotatable about a vertical axis.

4. The microscope according to claim 2, wherein the support comprises two essentially parallel side pieces.

5. The microscope according to claim 4, comprising control means for an electric actuation of microscope functions selected from the group consisting of a focus drive (FOCUS), a zoom drive (ZOOM) and drives for pivoting the microscope about the microscope swivel axis (X) and the beam divider exit axis (Y), the control means being disposed in at least one of the side pieces.

6. The microscope according to claim 2, wherein the support comprises transverse adjustment means for displacing adjoining support components in a horizontal direction relative to a longitudinal axis of the support.

7. The microscope according to claim 6, wherein the transverse adjustment means comprises a dovetail guideway.

8. The microscope according to claim 6, comprising rotating knobs for mechanically adjusting the transverse adjustment means.

9. The microscope according to claim 1, comprising handles mounted on the microscope for swiveling the microscope about the beam divider exit axis, the microscope swivel axis, and a vertical axis and for displacing the microscope in the direction of a horizontal axis.

10. The microscope according to claim 9, wherein the handles are disposed within the proximity of the center of gravity of the microscope.

11. The microscope according to claim 9, comprising electric drive means (14) for swiveling the microscope and for displacing the microscope.

12. The microscope according to claim 11, wherein one of the handles comprises means for activating the electric drive means (601, 602 and 603).

13. The microscope according to claim 11, wherein the electric drive means (14) for swiveling the microscope about the vertical axis comprises an electrically releasable brake (701).

14. The microscope according to claim 11, comprising means of keys (801) for engaging and disengaging the electric drive means.

* * * * *